United States Patent [19]

Bellis

[11] Patent Number: 4,853,485

[45] Date of Patent: Aug. 1, 1989

[54] METHOD FOR PRODUCING MONOMETHYLFORMAMIDE AND DIMETHYLFORMAMIDE

[75] Inventor: Harold E. Bellis, Wilmington, Del.

[73] Assignee: E. I. Du Pont de Nemours and Company, Wilmington, Del.

[21] Appl. No.: 112,017

[22] Filed: Oct. 21, 1987

Related U.S. Application Data

[63] Continuation of Ser. No. 603,908, Apr. 24, 1984, abandoned.

[51] Int. Cl.$^4$ .......................................... C07C 103/127
[52] U.S. Cl. .................................................. 564/215
[58] Field of Search ............................... 564/132, 215

[56] References Cited

U.S. PATENT DOCUMENTS

| | | | |
|---|---|---|---|
| 1,567,312 | 12/1925 | Wietzel | 564/132 |
| 2,204,371 | 6/1940 | Loder | 564/132 |
| 2,677,706 | 5/1954 | Giachino | 564/132 |
| 2,793,211 | 5/1957 | Cicero et al. | 564/132 X |
| 4,556,734 | 12/1985 | Knifton | 564/132 |

OTHER PUBLICATIONS

Groggins, "Unit Processes in Organic Synthesis", 3rd ed., pp. 541–543 (1947).
"A Study on High Pressure One-Step Synthesis of Dimethylformamide", Takezaki et al., Kogyo Kagaku Zasshi 63, 1739–1745 (1960).

*Primary Examiner*—Douglas W. Robinson
*Assistant Examiner*—Joseph A. Lipovsky
*Attorney, Agent, or Firm*—Craig H. Evans

[57] ABSTRACT

Monomethylformamide and dimethylformamide are produced by the catalytic reaction of formamide and methanol, using a quaternary ammonium compound as the catalyst.

3 Claims, No Drawings

METHOD FOR PRODUCING MONOMETHYLFORMAMIDE AND DIMETHYLFORMAMIDE

This application is a continuation of Ser. No. 603,908, field 4/24/87, now abandoned.

DESCRIPTION

1. Technical Field

This invention relates to a process for preparing monomethylformamide (MMF) and dimethylformamide (DMF). It is more particularly directed to such a process in which MMF and DMF are catalytically prepared from formamide and methanol.

2. Background and Summary of the Invention

DMF is a commodity in the chemical industry, widely used as a solvent. One of the common methods of preparing it is by the reaction of dimethylamine and carbon monoxide. This requires either a large plant for preparing the dimethylamine starting material, with its attendant huge investment (small plants are ordinarily uneconomical), or the large-scale purchase of dimethylamine on the open market, neither of which is satisfactory from an economic standpoint.

A satisfactory alternative would be a method whereby MMF and DMF are prepared by the reaction of formamide and methanol. Methanol is plentiful and inexpensive, and formamide is easily prepared from ammonia and carbon monoxide, both readily available and cheap.

The reaction of formamide and methanol to form MMF and DMF is known[1], but as described in the prior art is not practical on a commerical scale because of low yields.

I have now found that MMF and DMF can be prepared, easily and in good yield, by the catalytic reaction of formamide and methanol, using a particular quaternary ammonium compound as the catalyst.

DETAILED DESCRIPTION OF THE INVENTION

The catalyst used according to my invention is a quaternary ammonium compound represented by the structure

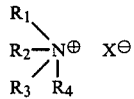

where
 $R_1$, $R_2$, $R_3$ and $R_4$ can be an alkyl radical of 1-12 carbon atoms;
 a hydroxy ethyl radical;
 a pyridyl radical; or
 a benzyl radical; and
 X can be Cl, Br, I, F or -OH.

[1]. See, for example, "A Study on High Pressure One-Step Synthesis of Dimethylformamide," Takezaki, Kitahama, Suzuki, Sugita and Yuasa, Kogyo Kagaku Zasshi 63, 1739-45 (1960).

Most quaternary compounds of this type are available in the marketplace. Those which are not can be made by the reaction of a tertiary amine and an alkyl halide as described in "Introduction to Organic Chemistry," Stretwieser and Heathcock, MacMillian Publishing Co., NY, 1976, page 777.

The quaternary compounds preferred for use according to the invention are tetramethyl ammonium bromide and tetraethyl ammonium iodide. Tetramethyl ammonium bromide is most preferred.

The reaction proceeds according to the equation

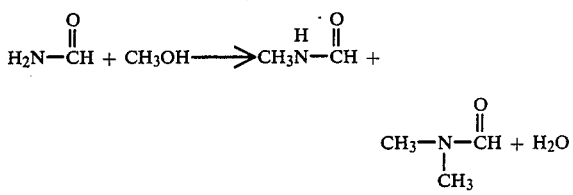

The reaction produces a mixture of MMF and DMF in proportions which can be varied as desired by changing the ratio of reactants (the reaction is stoichiometric, so use of two mols of methanol instead of one will produce more DMF instead of MMF).

The reaction can be run batchwise or continuously.

In the batch mode, the reactants are charged to a vessel in the desired proportion, together with the catalyst at a concentration of 0.1-5%, by weight of the reaction mass, preferably 0.5-1%. The reaction mass is then heated to and held at a temperature of 180°-275° C., preferably 225° C. Lower temperatures than this can be used, but the reaction proceeds at a much slower rate, as would be expected. Temperatures above 275° C. can also be used, but tend to promote the formation of undersirable by-products.

The reaction is run at autogenous pressure, normally 500-2000 psig (3447-13790 kPa).

When the reaction is complete, as determined bu periodic sampling and analysis by gas chromatography, the vessel is opened and the contents removed. The products, MMF and DMF, and any unreacted reactants present, can then be separated by conventional fractional distillation, and the MMF and DMF products further refined in the customary way if this is necessary.

The process can be run continuously under the same conditions. Formamide and methanol are fed into a suitable reactor which contains the catalyst on a suitable support. The amount of catalyst to be used, and the residence time of the reactants in the reactor, are dictated by the size of the reactor and the conditions under which the reaction is to be run, and can be easily determined according to conventional chemical engineering principles. MMF and DMF are withdrawn from the top of the reactor and then conventionally separated and refined.

When this continuous mode is run in series with a continuous process for preparing formamide from ammonia and carbon monoxide, the combination provides an efficient two-stage process for making MMF and DMF directly from those reactants.

EXAMPLES

Those skilled in the art will be able to practice this invention more easily after referring to the following illustrative examples.

These artisans will no doubt be able to compose numerous variations on the themes disclosed, such as changing the amounts of reactants slightly but insignificantly from those shown, substituting equivalent or nearly equivalent reactants for those shown, or adding innocuous substances. All these variations are considered to be part of the inventive concept.

In the Examples, all parts and percentages are by weight.

EXAMPLE 1

A reactor was charged with
Methanol: 130 parts
Formamide: 30 parts
Tetramethyl ammonium bromide: 4 parts The temperature of the reaction mass was raised to 225° C. over a period of 30 minutes and held at that temperature for 120 minutes, with stirring. Samples were withdrawn after 0, 20, 40, 60, 90 and 120 minutes and analyzed by gas chromatography for formamide, monomethylformamide and dimethylformamide content, as a percent of the reaction mass.

The results are shown in the following table:

| Minutes | % Formamide | % MMF | % DMF |
| --- | --- | --- | --- |
| 0 | 19.2 | 1.4 | 0.0 |
| 20 | 12.9 | 10.5 | 0.6 |
| 40 | 8.7 | 15.5 | 1.6 |
| 60 | 6.1 | 18.6 | 3.0 |
| 90 | 4.3 | 20.8 | 4.7 |
| 120 | 2.8 | 20.7 | 6.2 |

EXAMPLE 2

The process of Example 1 was repreated, using tetraethyl ammonium iodide instead of tetramethyl ammonium bromide.

The results are shown in the following table:

| Minutes | % Formamide | % MMF | % DMF |
| --- | --- | --- | --- |
| 0 | 19.8 | 1.5 | 0.1 |
| 20 | 12.1 | 9.9 | 0.6 |
| 40 | 9.4 | 14.6 | 1.6 |
| 60 | 7.1 | 18.0 | 2.7 |
| 90 | 4.7 | 18.9 | 4.5 |
| 120 | 3.0 | 19.4 | 6.3 |

EXAMPLE 3

The process of Example 1 was repeated, using as a charge
Methanol: 140 parts
Formamide: 40 parts
Cetyl dimethyl benzyl ammonium chloride: 2 parts Samples were withdrawn from the reactor after 0, 60, 90, and 150 minutes and analyzed.

The results are shown in the following table:

| Minutes | % Formamide | % MMF | % DMF |
| --- | --- | --- | --- |
| 0 | 29.9 | 0.7 | 0.0 |
| 60 | 22.1 | 11.1 | 0.6 |
| 90 | 15.9 | 16.4 | 1.3 |
| 150 | 6.6 | 22.6 | 5.0 |

I claim:

1. In the preparation of monomethylformamide and dimethylformamide by the catalytic reaction of formamide and methanol, the improvement comprising using as the catalyst a quaternary ammonium compound represented by the structure

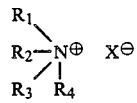

where
R$_1$, R$_2$, R$_3$ and R$_4$ can be an alkyl radical of 1-12 carbon atoms;
a hydroxy ethyl radical;
a pyridyl radical; or
a benzyl radical; and
X can be Cl, Br, I, F or -OH, said reaction being run without the utilization of carbon monoxide.

2. The process of claim 1 in which the catalyst is tetramethyl ammonium bromide.

3. The process of claim 1 in which the catalyst is tetracethyl ammonium iodide.

* * * * *